Figure 1:
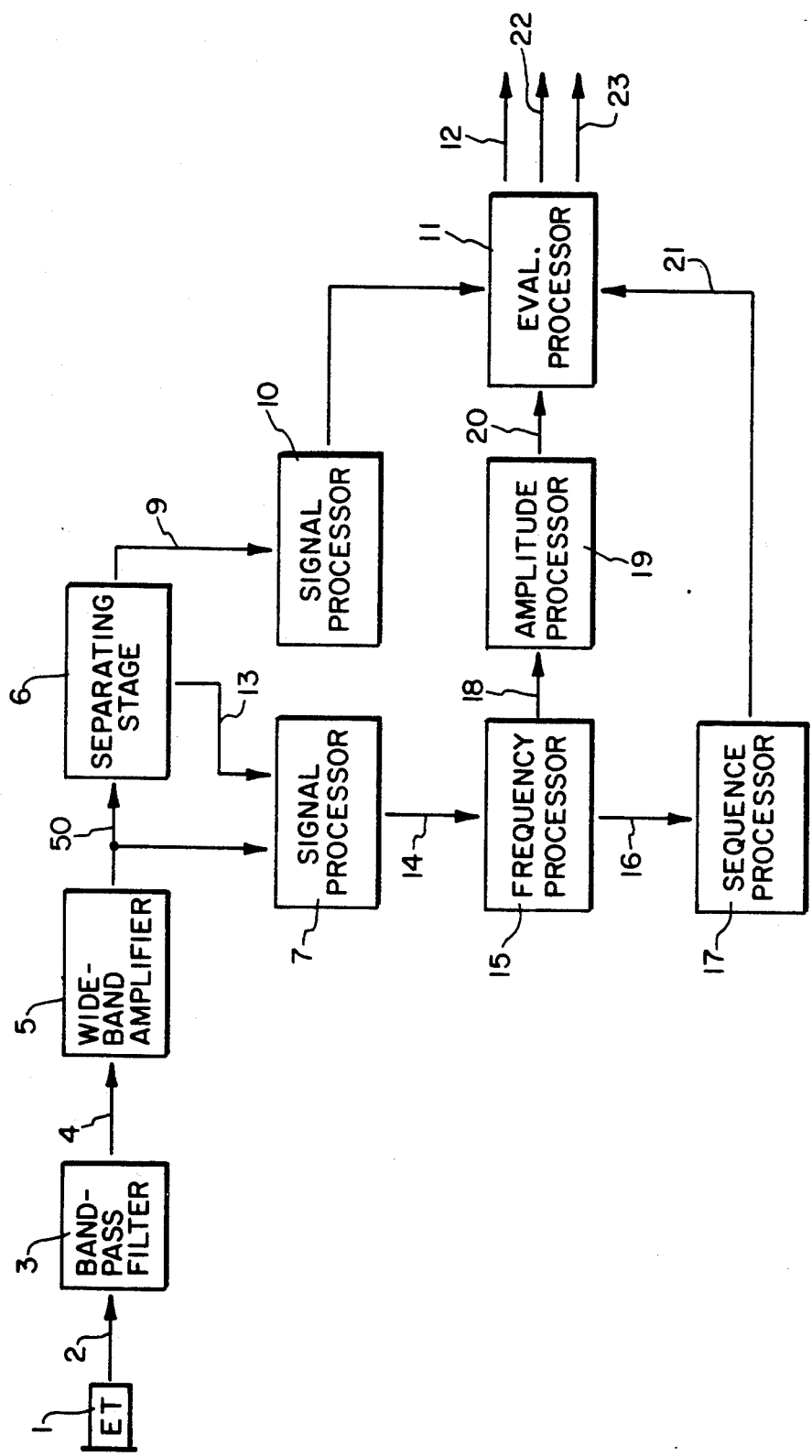

United States Patent [19]
Waschkies et al.

[11] Patent Number: 5,159,836
[45] Date of Patent: Nov. 3, 1992

[54] PROCESS AND DEVICE FOR MONITORING THE CHIP-REMOVING TREATMENT OF A WORKPIECE

[75] Inventors: Eckhard Waschkies, Blieskastel; Klaus Hepp, Rubenheim, both of Fed. Rep. of Germany

[73] Assignee: Fraunhofer-Gesellschaft zur Forderung Der Angewandten Forschung E.V., Munich, Fed. Rep. of Germany

[21] Appl. No.: 582,870

[22] PCT Filed: Sep. 2, 1989

[86] PCT No.: PCT/DE89/00572
§ 371 Date: Oct. 17, 1990
§ 102(e) Date: Oct. 17, 1990

[87] PCT Pub. No.: WO90/02944
PCT Pub. Date: Mar. 22, 1990

[30] Foreign Application Priority Data
Sep. 2, 1988 [DE] Fed. Rep. of Germany ....... 3829825

[51] Int. Cl.$^5$ .............................................. G01N 29/14
[52] U.S. Cl. ...................................... 73/587; 73/104; 73/660; 340/680; 340/683
[58] Field of Search ................ 73/587, 584, 579, 645, 73/646, 647, 648, 104, 660; 364/508, 551.02, 474.17; 340/679, 680, 683

[56] References Cited
U.S. PATENT DOCUMENTS

| | | | |
|---|---|---|---|
| 4,332,161 | 6/1982 | Kakino | 73/104 |
| 4,413,507 | 11/1983 | Drew et al. | 73/587 |
| 4,636,779 | 1/1987 | Thomas et al. | 340/680 |
| 4,636,780 | 1/1987 | Thomas et al. | 340/680 |
| 4,642,617 | 2/1987 | Thomas et al. | 340/680 |
| 4,707,687 | 11/1987 | Thomas et al. | 340/680 |
| 4,707,688 | 11/1987 | Thomas | 340/680 |
| 4,831,365 | 5/1989 | Thomas et al. | 340/680 |
| 4,849,741 | 7/1989 | Thomas | 340/680 |
| 4,918,427 | 4/1990 | Thomas et al. | 340/680 |

FOREIGN PATENT DOCUMENTS 0215268 3/1987 European Pat. Off. .
0244856 12/1985 Japan .
1182570 8/1986 Japan .

*Primary Examiner*—Hezron E. Williams
*Assistant Examiner*—Rose M. Finley
*Attorney, Agent, or Firm*—Baker & Daniels

[57] ABSTRACT

A process and device for monitoring the chip-removing treatment of a workpiece by analyzing the sound emission detectable on the tool which is transformed into an electrical signal, filtered, and compared with respect to its amplitude determined over a predetermined period of time with a predetermined adaptable threshold value. The constituents contained in the sound emission signal of the continuous basic noise signal resulting from the cutting and friction noise, and of the pulse-type chip-break signals superposed with respect to this with a higher amplitude, are separated and separately analyzed and evaluated.

20 Claims, 2 Drawing Sheets

PROCESS AND DEVICE FOR MONITORING THE CHIP-REMOVING TREATMENT OF A WORKPIECE

The invention relates to a process for monitoring the chip-removing treatment of a workpiece, especially in lathe-turning, by analyzing the sound emission detectable on the tool, which is transformed with the aid of an electroacoustic transformer into an electrical sound-emission signal, which is filtered and compared with respect to its amplitude determined over a predetermined period of time with a predetermined adaptable threshold value.

Furthermore, the invention relates to a device for the execution of the process with an electroacoustic transformer arranged on the tool holder, converting the sound emission signal, which transformer, over a high-pass filter, an amplifier and a detector, feeds a mean-value former, the output signal of which feeds the first input of a comparator, the second input of which is actable-upon with a threshold value voltage.

Such a process and such a device are known from U.S. Pat. No. 4,332,161 and make it possible to generate an output signal on the output of a comparator when the tool wear has exceeded a prescribed degree. Since the sound-emission signal contains pulse-type chip-break signals, the frequency and amplitude of which do not associate directly and clearly with the tool wear and the processing quality, the output voltage of the integrator and, therefore, the switching-over of the comparator cannot be dependably allocated to a predetermined wear on the tool. The voltage standing on the output of the integrator does not change in dependence on the chip-break sequence and, therefore, is no dependable measure for the tool wear.

Proceeding from this state of the art, underlying the invention is the problem of creating a process and a device which makes it possible dependably to detect exactly all forms of wear and dependably to evaluate the chip-break behavior.

This problem is solved according to the invention in the process mentioned at the outset by the means that the constituents contained in the sound emission signal of the continuous basic noise signal resulting from the cutting noise and friction noise, on the one hand, and of the pulse-type chip-break signals superposed with respect to this with a higher amplitude, on the other hand, are separated and separately analyzed and also evaluated.

Included is the evaluation and monitoring of mean values, distribution of amplitudes, and of energies of impulses of chip break signals in order to monitor fluctuations of characteristic values of the processed workpiece and/or chip temperature changed in consequence of tool wear.

According to the invention there is continuously formed a noise mean value of the sound emission signal, in which, however, for the mean value formation there are not taken into account by blending-out those values of the sound emission signal which arise during the time windows allocated to the chip-break signals.

A device for the execution of the process is characterized in that to the mean-value former there is allocated a switch-over arrangement by which the feed of the mean-value former with the sound emission signal is interruptable during the pulse-type chip-break signals.

Through the fact that for the evaluation of the tool wear and of the processing quality the characteristic signal constituents are separated and separately analyzed as well as statistically evaluated, there is achieved a high dependability in the evaluation and the monitoring resulting therefrom.

Expedient embodiments and further developments of the invention are the object of subclaims.

In the following, the invention is explained in detail with the aid of an example of execution represented in the drawing.

Figure 2:
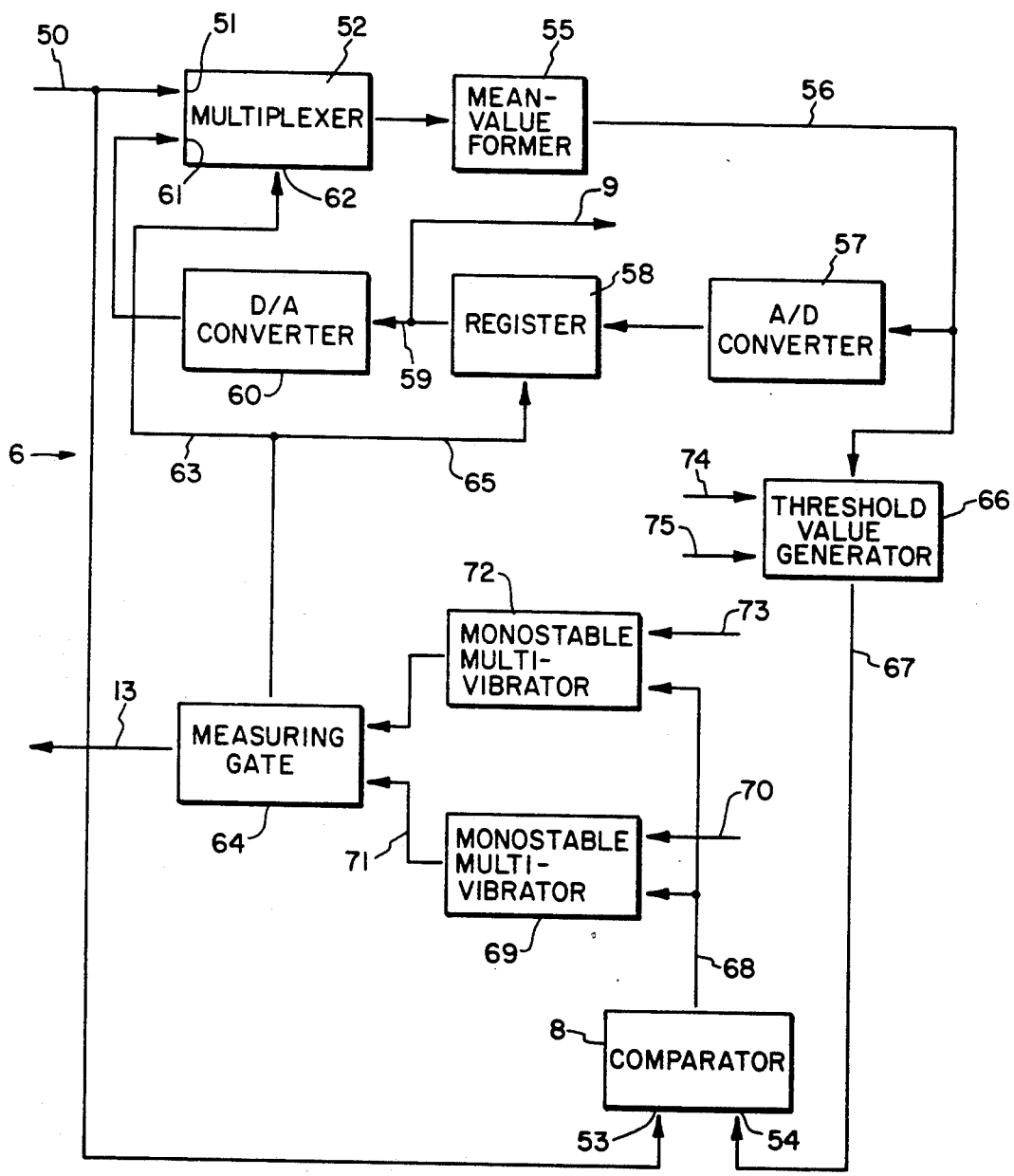

FIG. 1 shows a block circuit diagram of a sound-emission analysis apparatus according to the invention and FIG. 2 shows a block circuit diagram of the separating stage of the sound-emission analysis apparatus of the invention.

The sound emission analysis apparatus represented overall in the block circuit diagram in FIG. 1, for the monitoring of the chipping behavior and of the tool wear in a chip-removing treatment, especially in lathe turning, makes it possible to evaluate the processing quality and the quality of the turning process by the means that the sound emission generated by several different physical processes in the turning is detected and processed. The sound emission to be evaluated is received in a wide band on the tool holder with an electroacoustic transformer 1 represented schematically in FIG. 1. The electroacoustic transformer 1 is wide-banded and consists, for example, of a piezoelectric probe. The band width of the transformer extends from 20 kHz to 2 MHz.

The transformer 1 transforms the sound emission arising in the turning process into an electric signal, which passes over a line 2 to a band-pass filter 3. The electric sound emission signal arriving at the band pass filter 3 contains signal components which are triggered by the plastic deformation of the cutting edge, by frictional processes between the workpiece and the tool, by frictional processes between the generated chip and the tool, by breaking of the chips and by breakage processes on the tool (tool break-outs).

Through the breaking of the chips there arise pulse-type chip-break signals whose amplitude peaks are greater than the level of a continuous basic noise signal that arise from a cutting noise and a frictional noise by reason of the above-mentioned physical processes.

The band pass filter 3 serves to attenuate the lower-frequency signal constituents of the chip-break signals to such an extent that no overlapping of the individual chip break signals takes place any longer, which are very wide-banded and whose lower-frequency constituents run back and forth relatively weakly damped in the tool holder and, therefore, determine the signal duration of the chip break signals. In the case of high chip break sequences, without use of a filter, there could occur undesired overlappings of the individual impulses of the chip break signals, which hampers their evaluation.

The band pass filter 3 is preferably adjustable to a lower limit frequency between 20 and 500 kHz. The upper limit frequency of the band pass filter 3 amounts to about 2 MHz. In order to detect the individual impulses of the chip break signals as well as possible it is provided that the band pass filter 3 is adjusted in dependence on the manufacturing parameters and the material to be processed onto in each case the most favorable mid-frequency. In the case of brittle materials as well as in the case of short chips it is expedient to raise the mid-frequency, while with ductile materials and long chips a lowering of the mid-frequency is expedient. In addition to the perception of the individual pulses of the chip break signals, the band pass filter 3 also serves to damp the machine noises.

The filtered sound emission signal, which is composed of the continuous background noise signal and the pulse-type chip break signals passes over an amplifier input line 4 to a wide-band amplifier 5. The wide-band amplifier 5 serves, on the one hand, to amplify the sound emission signal to the voltage requisite for the further processing. Furthermore, the wide-band amplifier 5 contains a detector or amount-former in the form of a two-way rectifier or a squaring circuit when the subsequent stages need analog input signals, or an analog-digital converter when the succeeding stages are realized in digital technique.

The output of the wide-band amplifier 5 feeds the signal inputs of a separating stage 6 and of a chip break signal processor 7.

The separating stage 6 makes it possible to separate the pulse-type chip break signals contained in the sound emission signal from the continuous background noise signal. Use is made there of the fact that the pulse-type chip break signals present amplitude peaks that substantially exceed the background noise signal. The separating stage represented in FIG. 2 has at its disposal a comparator 8, which compares the amplified sound emission signal with a threshold value signal. The threshold value signal always lies above the level of the background noise signal, so that only the impulses of the pulse-type chip break signals shift the comparator output in each case from the first state into a second state. It is possible, accordingly, to detect and to separate or blend out the individual impulses of the chip break signals.

The threshold value signal fed to the comparator 8 of the separating stage 6 adapts itself automatically to the particular signal relations. For this it is provided that the threshold value signal is derived from the sound emission signal by a mean-value formation, in which the sound emission signal values remain unconsidered during the arising of the pulse-type chip break signals. Thereby the threshold value signal adapts itself automatically, independently of the chip break signals, to the level of the particular continuous background noise signal, for through the blending-out of the impulses of the chip break signals it is achieved that changes of the impulse amplitude or of the frequency of the chip break signals remain without influence on the threshold value signal. The threshold value signal fed to the comparator 8 of the separating stage 6 is generated by the means that the sound emission signal is averaged in each case over a prescribed space of time, in which process, however, in the mean-value formation the impulses of the chip break signals are blended out, i.e. not taken into consideration.

Such a separation of the noise signal allocated to the cutting and friction noises and the chip break signals allocated to the breaking of the chips is expedient, because the two signal constituents can change independently of one another. For the formation of the threshold value signals the impulses of the chip break signals are blended out, since their consideration in the averaging of the sound emission signal over a predetermined period of time would lead to a little usable signal, because changes of the level of the background noise signal and of the impulse amplitudes of the chip break signals can occur with differing strength and even in different directions.

The separating stage 6 contains a keyable (tastbaren) integrator or mean-value former, which continuously delivers the mean value, for example the RMS value, of the background noise signal determined over a predetermined span of time, as an averaging of the sound emission signal occurs under blending-out of the time segments that are allocated to the impulses of the chip break signals. Further details of the function of the construction of the separating stage 6 are further explained below with the aid of FIG. 2.

The separating stage 6 feeds, over a first output and a background noise signal line 9, a background noise signal processor 10 with data which are independent of the chip break sequence frequency and the impulse amplitudes of the chip break signals.

The background noise signal processor 10 carries out a statistical analysis of the averaged background noise signal. For this the averaged background noise signal is first parametrized, as in predictable time intervals the mean signal level of the background noise signal as well as the frequency of the dominating spectral constituent in the background noise signal are determined. Furthermore the background noise signal processor makes possible the determination of the distribution function of the spectral main constituents of the background noise, and the distribution function of the level of the background noise signal averaged over predictable time intervals as well as the scatter widths derivable therefrom. The distribution of the averaged background (basic) noise level is determined there, for example, over a time between 1 and 10 seconds. The width of the distribution function of the averaged background noise level is a measure for the free-surface and/or erosion wear.

The background noise signal processor 10 determines not only the frequency distribution of the averaged background noise level but also makes it possible to analyze this by determining the respective maximum, the width, the steepness, the excess and other magnitudes.

The data generated by the background noise signal processor 10 on the basis of the background noise signal determined in each case over 10 microseconds to 1 millisecond, feed an evaluation processor 11, which serves also as evaluating unit. The evaluating processor 11 monitors in particular whether the distribution of the averaged background noise signal level exceeds a prescribed width. If this is the case, then over a wear output line 12 a corresponding output signal is delivered for the further processing or for the breaking-off of the processing of the workpiece in consequence of excessively high tool wear. Also if the mean signal level or the frequency of the dominant spectral constituent shows a wear on the tool which is clamped in the tool holder provided with the converter 1, a signal is delivered on the wear output line 12 by the evaluating processor 11.

In order to improve the monitoring of the tool wear and to make it especially dependable, as well as for the monitoring of the chipping behavior, besides the evaluatation of the separated as well as averaged background noise signal there is provided an analysis and evaluation of the chip break signals.

The chip break signal processor 7 processes, therefore, only the sections of the sound emission signal allocated to the chip break signals. In order to analyze the time course of the pulse-type chip break signals, the chip break signal processor 7 has at its disposal an internal clock which makes it possible, in particular, to determine the arrival times and the signal durations of the chip break signals. Besides the parameters mentioned, the chip break signal processor 7 determines also the peak amplitudes of the pulse-type chip break signals.

The burst signal parameters determined by the chip break signal processor 7 pass over a processor output line 14 to a frequency processor 15, which makes possible a statistical analysis of the various signal parameters and, in particular, distribution functions of the various parameters mentioned.

Since the chip break signal processor 7 determines the arrival times and signal durations of the chip break signal impulses, the frequency processor 15 makes it possible to determine a distribution function of the time intervals between the individual impulses of the chip break signals. The determined frequency distribution shows that the chip break signals consist in each case of a signal group with several individual impulses. To each chip break there is allocated a signal group, the chip break sequence determining the spacings between the signal groups.

From the distribution function of the intervals of the impulses of the chip break signals there is defined by the frequency processor 15 a signal spacing filter. All the individual impulses of the chip break signals whose time spacings to the following individual impulse are shorter than a value determined from the signal spacing distribution function are grouped into signal groups with the aid of the frequency processor 15.

In the frequency processor 15 the time spacings are determined of the individual signal groups, in which process, for example, the time spacing is detected for the in each case last signal of a group to the last signal of the next group. The values of the time spacings of the signal groups which correspond to the time spacings between the chip breaks are fed for statistical analysis over a first output line 16 to a chip break sequence processor 17.

Over a second output line 18 the frequency processor 15 determines frequency distributions of the signal amplitudes in the form of a distribution function of the peak amplitudes of the individual impulses in the chip break signals. The distribution function of the peak amplitudes is evaluated in an amplitude processor 19 which, according to a further development of the process on which the sound emission analysis apparatus represented in FIG. 1 is based, processes, in addition to the distribution function of the amplitudes, also a distribution function of the energies of the pulse-type chip break signals. For this in the chip break signal processor 7 there are determined not only the maximal amplitudes of the individual impulses or bursts but also their energies, which are yielded in each case from the time integral of the amplitude squares over the duration of an individual impulse.

The amplitude processor 19 makes it possible to analyze the amplitude distribution supplied to it of the chip break signals in a special manner. There, for an assignable amplitude interval which extends from small amplitudes up to an amplitude below the maximally appearing amplitude, without consideration of the amplitudes lying over it, an approximation function (best fit process) is determined. By reason of this function derived from the actually occurring amplitude distribution there is then calculated the number of signals that should appear above a limit value on the basis of this distribution function. The amplitude processor 19 obtains, however, over the second output line 18, also the information regarding the actual number of signals with amplitudes above the limit value mentioned. In the amplitude processor 19 both values are compared with one another, i.e it is examined whether the number of signals amplitudes above the limit values corresponds to the number which can be calculated from the amplitude distribution of the signals below the limit value. If the actual number of signals with amplitudes above the limit value is substantially greater than it ought to be on the basis of the distribution function in the lower amplitude range, this is an indication of tool break-outs in the cutting surface. The number of amplitudes that exceed the certain limit value mentioned is fed over an amplitude line 20 to the evaluating processor 11.

The evaluation processor 11, accordingly, monitors not only parameters of the background noise signal in the above-described manner, but also parameters derived from the chip break signals.

As is perceived in FIG. 1, the evaluating processor 11 has at its disposal, in addition to the input line allocated to the background noise signal and the amplitude line 20, a third input line 21, which stands in connection with the output of the chip break sequence processor 17. In this manner the evaluating processor 11 obtains not only the distribution function of the continuous background noise as well as the number of amplitudes that exceed a certain limit value, but also information in regard to the chip break sequence frequency determined by the chip break sequence processor 17.

The chip break sequence processor 17 determines for this, for in each case assignable spaces of time, the frequency distribution of the time spacings of the signal groups. Furthermore, the chip break sequence processor 17 serves to carry out an analysis of this distribution function, there being evaluated the maximum of the distribution function, its width, etc.

The time spacings between the signal groups correspond to the time spacings between the chip breaks. For this reason the frequency distribution or the distribution function of the spacings of the signal groups corresponds to the distribution function of the chip break sequence and is accordingly, with known processing parameters, a measure for the chip lengths. Since the tool wear (free-surface and erosion wear) correlates with a change of the chip lengths, from the statistical parameters of the chip break spacing distribution function with the aid of the evaluating processor 11 there can be determined and evaluated the tool wear. For this, over the third input line 21 the characteristic values of the distribution of the chip break sequence (maximum, width etc) are passed on to the evaluating processor 11.

According to one embodiment it is provided that in the evaluating processor 11, for the different distribution functions of the diverse signal parameters there are stored model distributions which are compared with the determined distribution functions. For this, deviations in the statistical moments are determined. The results of the distribution functions as well as their deviations from model distributions form the basis for the evaluation of the chipping behavior and of the tool wear by the evaluating processor 11.

Besides the wear output 12, the evaluating processor 11 has a disturbance output 22 to indicate a disturbance in the case of contradictory input magnitudes of the evaluating processor 11, as is the case, for example, with a chip jam (Spanklemmer) when a rising wear noise occurs despite constant chip break sequence.

The evaluating processor 11 has at its disposal, further, a documentation output 23, by which there occurs a documentation and issuing of the input magnitudes of the evaluating processor 11 as document for the quality of the operating process.

One of the functions that is carried out by the evaluating processor 11 consists in a comparison of the input magnitudes with prescribed limit values (model distributions). On deviations between the desired and actual values, in the manner given in the following there is indicated a disturbance of the turning process or a wear on the tools.

If over the third input line 21 there are delivered signal numbers per time unit that lie outside the prescribed limit values there occurs a machine stop, since obvious tool break-outs are present.

If over the third input line 21 signal numbers per time unit are delivered that lie outside the prescribed limit values, and the values on the input connected with the amplitude line 20 likewise lie outside the limit values, a tool change is necessary, since wear marks are being exceeded.

If the values delivered from the background noise signal processor 10 lie outside the limit values, but the values of the amplitude line 20 lie within the admissible limits, then this means a disturbance of the process, for example a chip jam (Spanklemmer). This would have to be treated like, say, an empty supply maintenance of tools or the like.

The component groups described in connection with FIG. 1 can be realized in various manners. In particular, this is possible by permanently wired units or by separate programmable processors. There it is also possible to group several processors together into a programmable processor.

The separating stage 6 which generates a threshhold value voltage adapting itself to the background noise in order to make possible a blending-out of the impulses of the chip break signals independently of their amplitude and frequency, is described in detail in the following with the aid of an example of an analog solution represented in FIG. 2.

The separating stage 6 containing the comparator 8 and represented in FIG. 2 as a block circuit diagram is connected over an input line 50 with the output of the wide-band amplifier 5. By reason of the output signals of the wide-band amplifier 5 arriving over the input line 50 the separating stage 6 generates an averaged background noise signal which is decoupled over the background noise signal line 9. The chip break signal processor 7 represented in FIG. 1 is connected, on the one hand, to the output of the wide-band amplifier 5 and, on the other hand, over the measuring gate signal line 13 represented in FIGS. 1 and 2 with the separating stage 6.

The input line 50 connects the output of the wide-band amplifier 5, on the one hand, with the first input 51 of a multiplexer 52 and, on the other hand, with the signal input 53 of the comparator 8, whose comparison input 54 is acted upon with a threshold value signal which is generated in the manner yielded from the following description.

The output of the multiplexer 52 is connected with the input of a mean-value former 55 which integrates the signal fed in over the multiplexer 52, in particular the continuous background noise signal, or averages the same. The mean-value formation occurs there over a prescribed period of time. The signal averaging can occur in such a way that an RMS-value formation occurs. The mean-value former 55 can be realized by an RC member or, in the case of a digital solution in place of the analog solution represented in FIG. 2, a computer with an accumulator and a dividing member by which the mean value of a prescribed number of scanning values of the input signal is determined.

The mean-value former 55 represented in FIG. 2 delivers over an output line 56 an analog mean-value signal, the magnitude of which is determined by the amplitudes of a prescribed interval of time. This time interval is given, for example in the case of the realization by an RC member, by the magnitude of the integration capacitor.

The output line 56 is connected with the input of an analog/digital converter 57, which converts the analog mean value into a digital mean value and passes it on to a register 58 for temporary storage. The register 58 forms a digital scanning and holding circuit, by which inter alia there is prevented a vibrating of the system. The output of the register 58 is connected with the background noise signal line 9 over which the in each case actual mean value of the background noise signal to the background noise signal processor 10 is decouplable. Over a coupling line 59 the digitalized and averaged background noise signal passes to a digital/analog converter 60, the output of which is connected with the second input 61 of the multiplexer 52.

The multiplexer 52 is switchable over a control input 62 so that, at will, the signal lying on the first input 51 or the signal lying on the second input 61 can be switched through to the mean-value former 55. The arrangement of the separating stage 6 is made there in such a way that the first input 51 is always switched through if the continuous background noise signal is present alone, while on arising of the chip break signals the multiplexer 52 is switched over so that during the period of the arising of the chip break signals the averaged background noise signal remains constant and is fed back to the mean-value former and the chip break signals arising during this time do not influence the mean value on the output line 56 and the background noise signal line 9. In addition, the background noise signal processor engaged on outlet side of the separating stage 6 is temporarily deactivated. The switch-over of the multiplexer 52 and of the background noise signal processor 10 occurs over a control line 63 which is connected with the output of a measuring gate 64, which likewise generates a control signal for the register 58 and is connected with the register 58 over a control line 65. Every time when the pulse-type chip break signals arise the measuring gate 64 generates the allocated signals, in which process over the control line 63 there occurs a switch-over of the multiplexer 52 to the second input 61 and over the measuring gate signal line 13 a freeing of the chip break signal processor 7.

The analog threshold value voltage fed to the comparison input 54 of the comparator 8 is generated with the aid of a threshold value generator 66 which is connected with the comparator 8 over a threshold value line 67. The threshold value generator is acted upon input side over the output line 56 of the mean-value former 55 with (by ?) the averaged background noise signal. For the generation of the threshold value voltage this signal is prepared in a multiplication circuit and a following addition circuit. In the multiplication circuit the averaged background noise signal is multiplied with an experimentally determined peak factor which lies, for example, between 1.4 and 8. Thereupon there is added a constant offset voltage in order to generate the threshold value voltage for the comparator 8. In order to make it possible optimally to adapt the threshold value voltage fed to the comparator 8 to the particular conditions, the threshold value generator 66 has at its disposal an offset line 74 for the input of a constant offset and a peak value line 75 for the input of an experimentally determined crest factor.

As can be learned from FIG. 2, the measuring gate 64 for the switch-over of the multiplexer 52 and freeing of the chip break signal processor 7 is not controlled directly over the output line 68 of the comparator 8. Rather, the output line 68 is connected with a repeatedly startable monostable multivibrator 69 and an unrepeatedly startable monostable multivibrator 72. The monostable multivibrator 69 serves as delay circuit, the dead time of which is adjustable over a dead-time line 70 and lies between 10 $\mu$sec and 1 msec.

Each time when the sound emission signal on the signal input 53 of the comparator 8 exceeds the threshold value voltage on the comparison input 54, which is the case during the pulse-type chip break signals, the monostable multivibrator 69 is started. Over the switching line 71 the measuring gate 64 is opened, so that there occurs a switch-over of the multiplexer 52 to the second input 61 and a freeing of the chip break signal processor 7 occurs.

When the sound emission signal on the signal input 53 of the comparator 8 goes below the threshold value voltage on the comparison input 54 and the dead time of the monostable multivibrator 69 has expired, then over the switching line 71 the measuring gate 64 is again closed, so that a switch-over of the multiplexer 52 to the first input 51 occurs and a freeing of the background noise processor 10. This is the case at the end of each pulse-type chip break signal.

If during a chip break signal a sudden noise climb of the background noise signal occurs, the monostable multivibrator 52 prevents a blocking of the separating stage 6, as over the measuring gate 64 a switch-over of the multiplexer 52 to the first input 51 always occurs when, after the switch-over to the second input 61, a time has expired that is longer than the longest expected time for a pulse-type chip break signal. This down time lies on the order of 10 to 100 msec and is communicated to the monostable multivibrator 72 over a down-time line 73. The comparator 8, according, in each case on appearance of the chip break signal, switches on both monostable multivibrators 69 and 72, in which case normally, as is yielded from the above statements, in each case only the monostable multivibrator 69 brings about the switch-over process of the multiplexer 52.

We claim:

1. Process for the monitoring of the chip-removing treatment of a workpiece, especially in lathe turning, by analyzing the sound emission detectable on a tool comprising the steps of:
   transforming the sound emission with the aid of an electroacoustic transformer into an electrical sound emission signal;
   filtering the electrical sound emission signal;
   comparing the electrical sound emission signal with respect to its amplitude average over a prescribed period of time with a given adaptable threshold value;
   separating the electrical sound emission signal into a continuous background noise signal resulting from cutting noise and friction noise of the tool and pulse-type chip break signals superposed with respect thereto having a higher amplitude;
   separately analyzing the background noise signal and the pulse-type chip break signals; and
   evaluating the background noise signal and the pulse-type chip break signals.

2. Process according to claim 1, further comprising the step of:
   continuously forming a noise mean value of the electrical sound emission signal; and
   blending-out from the noise mean value the values of the sound emission that arise during time windows allocated to the pulse-type chip break signals.

3. Process according to claim 2, further comprising the step of:
   comparing the electrical sound emission signal with a threshold value signal which is derived from the noise mean value of the background noise signal for the separation of the pulse-type chip break signals and the background noise signal.

4. Process according to claim 1, further comprising the steps of:
   determining for the analysis of the pulse-type chip break signals and the background noise signal, at least one of a signal levels, signal parameters, and distribution functions of the signal parameters; and,
   evaluating individually or linked with one another, the pulse-type chip break signals and the background noise signal.

5. Process according to claim 4, further comprising the steps of:
   determining a chip break sequence frequency from the pulse-type chip break signals; and
   monitoring of the uniformity of quality of a turning process including detecting and analyzing constancy and scatter width of the chip break sequence frequency.

6. Process according to claim 4, further comprising the step of:
   evaluating and monitoring mean values and distributions of amplitudes and of energies of impulses of the pulse-type chip break signals in order to monitor fluctuations of material characteristic values of the processed workpiece and/or chip temperature changed in consequence of tool wear.

7. Process according to claim 4, further comprising the step of:
   analyzing, for evaluation of the tool wear or for the detection of tool break-outs, a signal level of the background noise signal outside of a time window defined by a sequence of impulses of the pulse-type chip break signals in the time and frequency ranges.

8. Process according to claim 7, further comprising the step of:
   determining a mean value of the amplitude average of the background noise signal over a prescribed time period.

9. Process according to claim 7, further comprising the step of:
   monitoring dominating spectral constituents of the background noise to detect tool break-outs.

10. Process according to claim 4, further comprising the step of:

determining changes of the material properties by detecting changes of pulse-type chip break signal parameters without simultaneous change of the level of the background noise signal.

11. Process according to claim 4, further comprising the step of:

linking the background noise signal parameters with the pulse-type chip break signal parameters.

12. Process according to claim 7, further comprising the step of:

examining whether changes occur both in the background noise signal and also in the pulse-type chip break signals in order to improve the dependability of the process evaluation in respect to the tool wear.

13. Process according to claim 4, further comprising the step of:

comparing distribution functions of the chip break sequence frequency, of the amplitudes, of the energies, of the rise times and signal durations of the pulse-type chip break signals, as well as distribution functions of the level and of the spectral constituents of the background noise with stored model distributions, in which the deviations from the model distributions are used as basis for evaluations of the chipping behavior and of the tool wear.

14. Process according to claim 4, further comprising the steps of:

detecting an amplitude distribution function of the impulses of the pulse-type chip break signals for a prescribable amplitude interval;

calculating, on the basis of the detected amplitude distribution function, the number of expected signals above a limit value lying outside a prescribable amplitude interval;

comparing calculated frequency value with the actually occurring number of impulses with amplitudes above the limit value, in which process a larger actual value than the calculated value is an indication of the tool break-outs in the cutting surface of the tool.

15. Apparatus for monitoring the chip-removing treatment of a workpiece by analyzing the sound emission detectable on a tool, the apparatus comprising:

an electroacoustic transducer arranged on a tool holder converting a sound emission into an electrical sound emission signal;

a high-pass filter coupled to said transducer;

an amplifier coupled to said high-pass filter;

a detector coupled to said amplifier;

a mean-value former having an input coupled to said detector and an output signal;

a comparator having a first input and a second input, wherein said mean-value output signal is coupled to and feeds said first input and said second input is acted upon with a threshold value voltage; and a switch-over arrangement by which the input of the mean-value former with the sound emission signal is interruptable during pulse-type chip break signals.

16. Apparatus according to claim 15, wherein the switch-over arrangement includes an input in which during the interruption of the feed with the sound emission signal, a feed occurs with the last-determined mean value of the sound emission signal freed from the chip break signals.

17. Apparatus according to claim 16 wherein the switch-over arrangement comprises a multiplexer coupled to the mean-value former said multiplexer having a first and second input, the first input of which multiplexer is connected with the detector and its second input is connected with a temporary storer in which the last-determined mean value in each case is stored.

18. Apparatus according to claim 15, wherein over the switch-over arrangement a chip break signal processor arrangement is driven, by which the chip break signals separated from the background noise signal of the sound emission signal are statistically analyzable.

19. Apparatus according to claim 15, wherein the mean-value former is connected with a background noise signal processor by which there is feasible a statistical analysis of the sound emission signal freed from the chip break signals.

20. Apparatus according to claim 18, wherein the chip break signal processor arrangement and the background noise signal processor feed an evaluating unit by which tool wear and also the processing quality are evaluable.

* * * * *